(12) United States Patent
Shuros et al.

(10) Patent No.: US 8,369,943 B2
(45) Date of Patent: *Feb. 5, 2013

(54) METHOD AND APPARATUS FOR NEURAL STIMULATION VIA THE LYMPHATIC SYSTEM

(75) Inventors: Allan C. Shuros, St. Paul, MN (US); Randy Westlund, River Falls, WI (US); Anthony V. Caparso, San Jose, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 70 days.

This patent is subject to a terminal disclaimer.

(21) Appl. No.: 12/604,233

(22) Filed: Oct. 22, 2009

(65) Prior Publication Data

US 2010/0042170 A1     Feb. 18, 2010

Related U.S. Application Data

(62) Division of application No. 11/422,421, filed on Jun. 6, 2006, now abandoned.

(51) Int. Cl.
*A61N 1/34* (2006.01)
(52) U.S. Cl. ............ 607/2; 607/9; 607/14; 607/42; 607/44; 607/45; 607/46; 607/115; 607/116
(58) Field of Classification Search .......... 607/2, 4, 607/5, 9, 39, 40, 42, 44, 115, 116
See application file for complete search history.

(56) References Cited

U.S. PATENT DOCUMENTS

| | | | |
|---|---|---|---|
| 3,814,080 A | 6/1974 | Norman | |
| 3,916,875 A | 11/1975 | Toch | |
| 4,650,467 A | 3/1987 | Bonello et al. | |
| 4,792,330 A | 12/1988 | Lazarus et al. | |
| 4,909,787 A | 3/1990 | Danforth | |
| 4,957,484 A | 9/1990 | Murtfeldt | |
| 5,107,834 A | 4/1992 | Ideker et al. | |
| 5,112,303 A | 5/1992 | Pudenz et al. | |
| 5,188,104 A | 2/1993 | Wernicke et al. | |
| 5,203,326 A | 4/1993 | Collins | |
| 5,203,348 A | 4/1993 | Dahl et al. | |
| 5,231,988 A | 8/1993 | Wernicke et al. | |

(Continued)

FOREIGN PATENT DOCUMENTS

| | | |
|---|---|---|
| EP | 1504778 A2 | 2/2005 |
| JP | 0355032 | 3/1991 |

(Continued)

OTHER PUBLICATIONS

"U.S. Appl. No. 11/422,414, Non-Final Office Action mailed Aug. 14, 2009", 18 pgs.

(Continued)

*Primary Examiner* — Carl H Layno
*Assistant Examiner* — Allen Porter, Jr.
(74) *Attorney, Agent, or Firm* — Schwegman Lundberg & Woessner, P.A.

(57) ABSTRACT

An implantable neural stimulation system includes an implantable medical device having a neural stimulation circuit and at least one implantable lead configured to allow one or more stimulation electrodes to be placed in one or more lymphatic vessels of a patient, such as the patient's thoracic duct and/or vessels branching from the thoracic duct. Neural stimulation pulses are delivered from the implantable medical device to one or more target regions adjacent to the thoracic duct or the vessels branching from the thoracic duct through the one or more stimulation electrodes.

26 Claims, 7 Drawing Sheets

U.S. PATENT DOCUMENTS

| | | | |
|---|---|---|---|
| 5,263,480 A | 11/1993 | Wernicke et al. |
| 5,284,153 A | 2/1994 | Raymond et al. |
| 5,305,745 A | 4/1994 | Zacouto |
| 5,333,609 A | 8/1994 | Bedingham et al. |
| 5,342,407 A | 8/1994 | Dahl et al. |
| 5,360,442 A | 11/1994 | Dahl et al. |
| 5,387,231 A | 2/1995 | Sporer |
| 5,391,143 A | 2/1995 | Kensey |
| 5,405,363 A | 4/1995 | Kroll et al. |
| 5,423,872 A | 6/1995 | Cigaina |
| 5,431,683 A | 7/1995 | Bowald et al. |
| 5,464,429 A | 11/1995 | Hedberg et al. |
| 5,468,254 A | 11/1995 | Hahn et al. |
| 5,496,362 A | 3/1996 | KenKnight et al. |
| 5,500,005 A | 3/1996 | Strandberg et al. |
| 5,522,853 A | 6/1996 | Kroll |
| 5,545,202 A | 8/1996 | Dahl et al. |
| 5,596,988 A | 1/1997 | Markle et al. |
| 5,603,732 A | 2/1997 | Dahl et al. |
| 5,655,548 A | 8/1997 | Nelson et al. |
| 5,658,318 A | 8/1997 | Stroetmann et al. |
| 5,662,689 A | 9/1997 | Elsberry et al. |
| 5,697,953 A | 12/1997 | Kroll et al. |
| 5,718,718 A | 2/1998 | Kroll et al. |
| 5,792,187 A | 8/1998 | Adams |
| 5,797,967 A | 8/1998 | KenKnight |
| 5,817,131 A | 10/1998 | Elsberry et al. |
| 5,817,138 A * | 10/1998 | Suzuki ............................. 607/67 |
| 5,827,326 A | 10/1998 | Kroll et al. |
| 5,836,976 A | 11/1998 | Min et al. |
| 5,865,744 A | 2/1999 | Lemelson |
| 5,891,084 A | 4/1999 | Lee |
| 5,893,881 A | 4/1999 | Elsberry et al. |
| 5,916,243 A | 6/1999 | KenKnight et al. |
| 5,954,752 A | 9/1999 | Mongeon et al. |
| 5,957,956 A | 9/1999 | Kroll et al. |
| 5,978,705 A | 11/1999 | KenKnight et al. |
| 6,024,704 A | 2/2000 | Meador et al. |
| 6,026,332 A | 2/2000 | Kenknight et al. |
| 6,032,079 A | 2/2000 | KenKnight et al. |
| 6,038,483 A | 3/2000 | KenKnight et al. |
| 6,077,227 A | 6/2000 | Miesel |
| 6,106,477 A | 8/2000 | Miesel et al. |
| 6,115,637 A | 9/2000 | Lennox et al. |
| 6,129,685 A | 10/2000 | Howard, III |
| 6,134,470 A | 10/2000 | Hartlaub |
| 6,152,955 A | 11/2000 | KenKnight et al. |
| 6,238,423 B1 | 5/2001 | Bardy |
| 6,272,370 B1 | 8/2001 | Gillies et al. |
| 6,275,730 B1 | 8/2001 | KenKnight et al. |
| 6,292,695 B1 | 9/2001 | Webster, Jr. et al. |
| 6,321,109 B2 | 11/2001 | Ben-Haim et al. |
| 6,347,247 B1 * | 2/2002 | Dev et al. .......................... 607/2 |
| 6,368,274 B1 | 4/2002 | Van Antwerp et al. |
| 6,370,417 B1 | 4/2002 | Horbaschek et al. |
| 6,400,982 B2 | 6/2002 | Sweeney et al. |
| 6,408,213 B1 | 6/2002 | Bartig et al. |
| 6,475,223 B1 | 11/2002 | Werp et al. |
| 6,535,764 B2 | 3/2003 | Imran et al. |
| 6,542,776 B1 | 4/2003 | Gordon et al. |
| 6,571,125 B2 | 5/2003 | Thompson |
| 6,574,514 B2 | 6/2003 | Partridge et al. |
| 6,584,362 B1 | 6/2003 | Scheiner et al. |
| 6,587,719 B1 | 7/2003 | Barrett et al. |
| 6,606,523 B1 | 8/2003 | Jenkins |
| 6,609,025 B2 | 8/2003 | Barrett et al. |
| 6,611,715 B1 | 8/2003 | Boveja |
| 6,615,084 B1 | 9/2003 | Cigaina |
| 6,629,534 B1 | 10/2003 | St. Goar et al. |
| 6,647,292 B1 | 11/2003 | Bardy et al. |
| 6,676,686 B2 | 1/2004 | Naganuma |
| 6,678,557 B1 | 1/2004 | Tumey |
| 6,684,104 B2 | 1/2004 | Gordon et al. |
| 6,692,490 B1 * | 2/2004 | Edwards ......................... 606/41 |
| 6,721,597 B1 | 4/2004 | Bardy et al. |
| 6,735,477 B2 | 5/2004 | Levine |
| 6,741,882 B2 | 5/2004 | Schaffter et al. |
| 6,804,558 B2 | 10/2004 | Haller et al. |
| 6,826,428 B1 | 11/2004 | Chen et al. |
| 6,835,194 B2 | 12/2004 | Johnson et al. |
| 6,842,648 B2 | 1/2005 | Partridge et al. |
| 6,865,416 B2 | 3/2005 | Dev et al. |
| 6,879,859 B1 | 4/2005 | Boveja |
| 6,889,076 B2 | 5/2005 | Cigaina |
| 6,893,429 B2 | 5/2005 | Petersen |
| 6,895,278 B1 | 5/2005 | Gordon |
| 6,918,873 B1 | 7/2005 | Millar et al. |
| 6,950,707 B2 | 9/2005 | Whitehurst |
| 6,952,610 B2 | 10/2005 | Ostroff et al. |
| 6,970,741 B1 | 11/2005 | Whitehurst |
| 6,974,448 B2 | 12/2005 | Petersen |
| 6,988,003 B2 | 1/2006 | Bardy et al. |
| 6,999,814 B2 | 2/2006 | Hauser et al. |
| 7,039,459 B2 | 5/2006 | Bardy et al. |
| 7,043,299 B2 | 5/2006 | Erlinger et al. |
| 7,069,080 B2 | 6/2006 | Bardy et al. |
| 7,076,294 B2 | 7/2006 | Bardy et al. |
| 7,123,961 B1 | 10/2006 | Kroll et al. |
| 7,167,751 B1 | 1/2007 | Whitehurst et al. |
| 7,198,603 B2 | 4/2007 | Penner et al. |
| 7,250,041 B2 | 7/2007 | Chiu et al. |
| 7,260,431 B2 | 8/2007 | Libbus et al. |
| 7,277,761 B2 | 10/2007 | Shelchuk |
| 7,295,877 B2 | 11/2007 | Govari |
| 7,317,941 B2 | 1/2008 | Stomberg et al. |
| 7,526,337 B2 | 4/2009 | Shuros et al. |
| 7,606,622 B2 | 10/2009 | Reeve |
| 7,616,991 B2 | 11/2009 | Mann et al. |
| 7,620,454 B2 | 11/2009 | Dinsmoor et al. |
| 7,734,341 B2 | 6/2010 | Shuros |
| 7,769,427 B2 | 8/2010 | Shachar |
| 7,774,055 B1 | 8/2010 | Min |
| 7,873,401 B2 | 1/2011 | Shachar |
| 7,894,906 B2 | 2/2011 | Allan |
| 7,966,057 B2 | 6/2011 | Macaulay |
| 8,116,883 B2 | 2/2012 | Williams et al. |
| 8,126,538 B2 | 2/2012 | Shuros et al. |
| 2001/0007924 A1 | 7/2001 | Kamada et al. |
| 2001/0037061 A1 | 11/2001 | Eckmiller et al. |
| 2001/0041870 A1 | 11/2001 | Gillis et al. |
| 2002/0016615 A1 | 2/2002 | Dev et al. |
| 2002/0029037 A1 | 3/2002 | Kim |
| 2002/0042630 A1 | 4/2002 | Bardy et al. |
| 2002/0068958 A1 | 6/2002 | Bardy et al. |
| 2002/0072780 A1 | 6/2002 | Foley |
| 2002/0082658 A1 | 6/2002 | Heinrich et al. |
| 2002/0087192 A1 | 7/2002 | Barrett et al. |
| 2002/0103510 A1 | 8/2002 | Bardy et al. |
| 2002/0111601 A1 | 8/2002 | Thompson |
| 2002/0123674 A1 | 9/2002 | Plicchi et al. |
| 2002/0156462 A1 | 10/2002 | Stultz |
| 2002/0188253 A1 | 12/2002 | Gordon et al. |
| 2003/0009202 A1 | 1/2003 | Levine |
| 2003/0018247 A1 | 1/2003 | Gonzalez |
| 2003/0036773 A1 | 2/2003 | Whitehurst et al. |
| 2003/0055463 A1 | 3/2003 | Gordon et al. |
| 2003/0074027 A1 | 4/2003 | Chen et al. |
| 2003/0078623 A1 | 4/2003 | Weinberg et al. |
| 2003/0105506 A1 | 6/2003 | Krishnan et al. |
| 2003/0113303 A1 | 6/2003 | Schwartz |
| 2003/0114895 A1 | 6/2003 | Gordon et al. |
| 2003/0144708 A1 | 7/2003 | Starkebaum |
| 2003/0181951 A1 | 9/2003 | Cates |
| 2003/0204185 A1 | 10/2003 | Sherman et al. |
| 2003/0212436 A1 | 11/2003 | Brown |
| 2004/0015193 A1 | 1/2004 | Lamson et al. |
| 2004/0015201 A1 | 1/2004 | Greenstein |
| 2004/0024428 A1 | 2/2004 | Barrett et al. |
| 2004/0039427 A1 | 2/2004 | Barrett et al. |
| 2004/0088022 A1 | 5/2004 | Chen |
| 2004/0098059 A1 | 5/2004 | Chen et al. |
| 2004/0102804 A1 | 5/2004 | Chin |
| 2004/0106953 A1 | 6/2004 | Yomtov et al. |
| 2004/0147976 A1 | 7/2004 | Gordon et al. |
| 2004/0158297 A1 | 8/2004 | Gonzalez |
| 2004/0162595 A1 | 8/2004 | Foley |
| 2004/0172080 A1 | 9/2004 | Stadler et al. |

| | | |
|---|---|---|
| 2004/0172088 A1 | 9/2004 | Knudson |
| 2004/0172102 A1 | 9/2004 | Leysieffer |
| 2004/0193229 A1 | 9/2004 | Starkebaum et al. |
| 2004/0193231 A1 | 9/2004 | David et al. |
| 2004/0210118 A1 | 10/2004 | Letort |
| 2004/0220629 A1 | 11/2004 | Kamath et al. |
| 2004/0230255 A1 | 11/2004 | Dobak, III |
| 2004/0243182 A1 | 12/2004 | Cohen et al. |
| 2005/0033376 A1 | 2/2005 | Whitehurst |
| 2005/0043675 A1 | 2/2005 | Pastore et al. |
| 2005/0043765 A1 | 2/2005 | Williams et al. |
| 2005/0043894 A1 | 2/2005 | Fernandez |
| 2005/0049472 A1 | 3/2005 | Manda et al. |
| 2005/0065553 A1 | 3/2005 | Ben Ezra et al. |
| 2005/0065575 A1 | 3/2005 | Dobak |
| 2005/0070974 A1 | 3/2005 | Knudson et al. |
| 2005/0075678 A1 | 4/2005 | Faul |
| 2005/0075701 A1 | 4/2005 | Shafer |
| 2005/0075702 A1 | 4/2005 | Shafer |
| 2005/0080346 A1 | 4/2005 | Gianchandani et al. |
| 2005/0080462 A1 | 4/2005 | Jenkins et al. |
| 2005/0090873 A1 | 4/2005 | Imran |
| 2005/0131464 A1 | 6/2005 | Heinrich et al. |
| 2005/0131486 A1 | 6/2005 | Boveja et al. |
| 2005/0143765 A1 | 6/2005 | Bachmann et al. |
| 2005/0143776 A1 | 6/2005 | Brown |
| 2005/0143787 A1 | 6/2005 | Boveja et al. |
| 2005/0149014 A1 | 7/2005 | Hauck et al. |
| 2005/0149141 A1 | 7/2005 | Starkebaum |
| 2005/0149142 A1 | 7/2005 | Starkebaum |
| 2005/0149157 A1 | 7/2005 | Hunter et al. |
| 2005/0187584 A1 | 8/2005 | Denker et al. |
| 2005/0222637 A1 | 10/2005 | Chen |
| 2005/0222638 A1 | 10/2005 | Foley et al. |
| 2005/0228471 A1 | 10/2005 | Williams et al. |
| 2005/0240239 A1 | 10/2005 | Boveja et al. |
| 2005/0240243 A1 | 10/2005 | Barolat et al. |
| 2005/0246006 A1 | 11/2005 | Daniels |
| 2005/0261741 A1 | 11/2005 | Libbus et al. |
| 2005/0267440 A1 | 12/2005 | Herman et al. |
| 2005/0273060 A1 | 12/2005 | Levy et al. |
| 2005/0288729 A1 | 12/2005 | Libbus et al. |
| 2005/0288730 A1 | 12/2005 | Deem et al. |
| 2006/0015164 A1 | 1/2006 | Partridge et al. |
| 2006/0020333 A1 | 1/2006 | Lashinski et al. |
| 2006/0030837 A1 | 2/2006 | McKenna et al. |
| 2006/0074453 A1 | 4/2006 | Kieval et al. |
| 2006/0116729 A1 | 6/2006 | Chen et al. |
| 2006/0136001 A1 | 6/2006 | Ortega et al. |
| 2006/0149331 A1 | 7/2006 | Mann et al. |
| 2006/0149337 A1 | 7/2006 | John |
| 2006/0217779 A1 | 9/2006 | Ransbury et al. |
| 2006/0247601 A1 | 11/2006 | Ellin et al. |
| 2006/0259077 A1 | 11/2006 | Pardo et al. |
| 2007/0021731 A1 | 1/2007 | Garibaldi et al. |
| 2007/0027460 A1 | 2/2007 | Case et al. |
| 2007/0027484 A1 | 2/2007 | Guzman et al. |
| 2007/0027500 A1 | 2/2007 | Maschino et al. |
| 2007/0244520 A1 | 10/2007 | Ferren et al. |
| 2007/0255340 A1 | 11/2007 | Giftakis et al. |
| 2007/0270675 A1 | 11/2007 | Kane et al. |
| 2007/0282376 A1 | 12/2007 | Shuros |
| 2007/0282380 A1 | 12/2007 | Brooke et al. |
| 2007/0282382 A1 | 12/2007 | Shuros et al. |
| 2007/0282386 A1 | 12/2007 | Shuros |
| 2007/0282390 A1 | 12/2007 | Shuros |
| 2008/0009719 A1 | 1/2008 | Shuros et al. |
| 2008/0058887 A1 | 3/2008 | Griffin et al. |
| 2008/0086185 A1 | 4/2008 | Amurthur et al. |
| 2008/0097412 A1 | 4/2008 | Shuros et al. |
| 2008/0260861 A1 | 10/2008 | Hagendoorn et al. |
| 2008/0294228 A1 | 11/2008 | Brooke et al. |
| 2009/0228059 A1 | 9/2009 | Shuros |
| 2010/0217346 A1 | 8/2010 | Shuros |
| 2010/0227807 A1 | 9/2010 | Stossel et al. |
| 2011/0106202 A1 | 5/2011 | Ding et al. |

FOREIGN PATENT DOCUMENTS

| | | |
|---|---|---|
| JP | 6113998 A | 4/1994 |
| JP | 2004-065529 A | 3/2004 |
| JP | 2004-524893 A | 8/2004 |
| JP | 2005532878 A | 11/2005 |
| SU | 1074527 A1 | 2/1984 |
| WO | WO-9314694 A1 | 8/1993 |
| WO | WO-03028542 A2 | 4/2003 |
| WO | WO-93/14694 A1 | 8/2003 |
| WO | WO-03/098177 A2 | 11/2003 |
| WO | WO-03098177 A2 | 11/2003 |
| WO | WO-2004/006795 A1 | 1/2004 |
| WO | WO-2004/032791 A2 | 4/2004 |
| WO | WO-2005/089863 | 9/2005 |
| WO | WO-2005/089863 A1 | 9/2005 |
| WO | WO-2005107862 A1 | 11/2005 |
| WO | WO-2007/067690 A2 | 6/2007 |
| WO | WO-2007/146489 A2 | 12/2007 |
| WO | WO-2007/146493 A1 | 12/2007 |
| WO | WO-2007/146517 A2 | 12/2007 |
| WO | WO-2008/030344 A2 | 3/2008 |

OTHER PUBLICATIONS

"U.S. Appl. No. 11/422,414, Response filed Dec. 14, 2009 to Non Final Office Action mailed Aug. 14, 2009", 7 pgs.

U.S. Appl. No. 11/422,417, Restriction Requirement Mailed Jul. 25, 2007, 5 pgs.

"U.S. Appl. No. 11/422,417, Non-Final Office Action mailed Apr. 21, 2008", 7 pgs.

"U.S. Appl. No. 11/422,417, Notice of Allowance mailed Dec. 12, 2008", 4 pgs.

"U.S. Appl. No. 11/422,417, Response filed Aug. 21, 2008 to Non Final Office Action mailed Apr. 21, 2008", 6 pgs.

"U.S. Appl. No. 11/422,417, Non-Final Office Action mailed Sep. 25, 2007", 7 pgs.

"U.S. Appl. No. 11/422,417, Response filed Aug. 27, 2007 to Restriction Requirement mailed Jul. 25, 2007", 4 pgs.

"U.S. Appl. No. 11/422,417, Response filed Jan. 25, 2008 to Non-Final Office Action mailed Sep. 25, 2007", 7 pgs.

"U.S. Appl. No. 11/422,418, Non-Final Office Action mailed Sep. 15, 2008", 11 pgs.

"U.S. Appl. No. 11/422,418, Response filed Dec. 15, 2008 to Non-Final Office Action mailed Sep. 15, 2008", 12 pgs.

"U.S. Appl. No. 11/422,418, Response filed Apr. 27, 2009 to Restriction Requirement mailed Mar. 25, 2009", 6 pgs.

"U.S. Appl. No. 11/422,418, Restriction Requirement mailed Mar. 25, 2009", 7 pgs.

"U.S. Appl. No. 11/422,418, Non-Final Office Action mailed Aug. 13, 2009", 8 pgs.

"U.S. Appl. No. 11/422,418, Response filed Nov. 13, 2009 to Non-Final Office Action mailed Aug. 13, 2009", 7 pgs.

"U.S. Appl. No. 11/422,421, Non-Final Office Action mailed Dec. 10, 2008", 16 pgs.

"U.S. Appl. No. 11/422,421, Advisory Action mailed Sep. 28, 2009", 5 pgs.

"U.S. Appl. No. 11/422,421, Final Office Action mailed Jul. 22, 2009", 15 pgs.

"U.S. Appl. No. 11/422,421, Response filed Apr. 9, 2009 to Non Final Office Action mailed Dec. 10, 2008", 12 pgs.

"U.S. Appl. No. 11/422,421, Response filed Sep. 17, 2009 to Final Office Action mailed Jul. 22, 2009", 9 pgs.

"U.S. Appl. No. 11/675,696, Non-Final Office Action mailed Sep. 30, 2009", 7 pgs.

"U.S. Appl. No. 11/675,696, Response filed Dec. 28, 2009 to Non Final Office Action mailed Sep. 30, 2009", 8 pgs.

"U.S. Appl. No. 11/675,696, Restriction Requirement mailed Jun. 2, 2009", 8 pgs.

"U.S. Appl. No. 11-675,696, Response filed Jul. 1, 2009 to Restriction Requirement mailed Jun. 2, 2009", 6 pgs.

"BIONTECH—The BION™ Technology Partnership", [online]. [archived Dec. 14, 2003]. Retrieved from the Internet: <URL: http://web.archive.org/web/20031214070040/www.biontech.org>, (2003), 4 pgs.

"European Application Serial No. 07797400.4, Communication mailed Apr. 21, 2009", 3 pgs.
"European Application Serial No. 07797400.4, Response filed Oct. 12, 2009 to Communication mailed Apr. 21, 2009", 10 pgs.
"International Application Serial No. PCT/US2007/068617, International Search Report mailed Mar. 10, 2008", 4 pgs.
"International Application Serial No. PCT/US2007/068617, Written Opinion mailed Mar. 10, 2008", 8 pgs.
"Japanese Application Serial No. 2009-514448, Amended Claims filed Feb. 6, 2009", (w/English Translation of Claims), 9 pgs.
"Physician's Manual—VNS Therapy™ Lead Model 302", Copyright 2003, 2004, 2005 Cyberonics, Inc., Houston, TX, (Jul. 2005), 35 pgs.
Amurthur, B., et al., "Distributed Neuromodulation System for Treatment of Cardiovascular Disease", U.S. Appl. No. 11/539,301, filed Oct. 6, 2006, 19 pgs.
Ando, M., et al., "Efferent vagal nerve stimulation protects heart against ischemia-induced arrhythmias by preserving connexin43 protein", *Circulation*, 112(2), (Jul. 12, 2005), 164-70.
Gray, H., et al., "2. The Thoractic Duct", *Anatomy of the Human Body*, (Philadelphia: Lea & Febiger), Bartleby.com 2000, [online]. Retrieved from the Internet: <URL: www.bartleby.com/107/176.html>, (1918), 3 pgs.
Issa, Z. F., et al., "Thoractic spinal cord stimulation reduces the risk of ischemic ventricular arrhythmias in a postinfarction heart failure canine model", *Circulation*, 111(24), (Jun. 21, 2005), 3217-20.
Knott, E. M., et al., "Increased lymphatic flow in the thoracic duct during manipulative intervention", *J Am Osteopath Assoc.*, 105(10), (Oct. 2005), 447-56.
Kouakam, C., et al., "Effect of elevated heart rate preceding the onset of ventricular tachycardia on antitachycardia pacing effectiveness in patients with implantable cardioverter defibrillators.", *American Journal of Cardiology*, 92(1), (Jul. 1, 2003), 26-32.
Lei, Y., et al., "Effects and Mechanisms of Implantable Gastric Stimulation on Gastric Distention in Conscious Dogs", *Obesity Surgery*, 15(4), (Apr. 2005), 528-533.
Murakawa, Y., et al., "Effect of Cervical Vagal Nerve stimulation on Defibrillation Energy: a Possible Adjunct to Efficient Defibrillation", *Japanese Heart Journal* 44(1), (Jan. 2003), 91-100.
Pulley, M. S., et al., "Intravenous, intralesional and endolymphatic administration of lymphokines in human cancer", *Lymphokine Research.*, vol. 5, Supplement 1, (1986), S157-S163.
Sobotta, J, et al., "The Membranous Labyrinth", *Atlas of Human Anatomy*, vol. III, W.B. Sauder Company, (2006), 1 pg.
Takahashi, N, "Vagal Modulation of Ventricular Tachyarrhythmias Induced by Left Ansae Subclaviae Stimulation in Rabbits", *Japanese Heart Journal*, 39(4), (Jul. 1998), 503-11.
Vanoli, E., et al., "Vagal Stimulation and Prevention of Sudden Death in Conscious Dogs With a Healed Myocardial Infarction", *Circulation Research*, 68(5), (May 1991), 1471-1481.
Zamotrinsky, A. V., et al., "Vagal neurostimulation in patients with coronary artery disease.", *Autonomic Neuroscience: Basic and Clinical*, 88(1-2), (Apr. 12, 2001), 109-116.
"U.S. Appl. No. 11/422,414, Final Office Action mailed Feb. 5, 2010", 16 pgs.
"U.S. Appl. No. 11/422,414, Non-Final Office Action mailed May 27, 2010", 10 pgs.
"U.S. Appl. No. 11/422,414, Notice of Allowance mailed Oct. 13, 2010", 7 pgs.
"U.S. Appl. No. 11/422,414, Response filed May 5, 2010 to Final Office Action mailed Feb. 5, 2010", 6 pgs.
"U.S. Appl. No. 11/422,414, Response filed Aug. 26, 2010 to Non Final Office Action mailed May 27, 2010", 6 pgs.
"U.S. Appl. No. 11/422,418, Notice of Allowance mailed Jan. 28, 2010", 8 pgs.
"U.S. Appl. No. 11/422,423 Non-Final Office Action mailed Jul. 21, 2010", 13 pgs.

"U.S. Appl. No. 11/422,423, Final Office Action mailed Apr. 9, 2010", 12 pgs.
"U.S. Appl. No. 11/422,423, Final Office Action mailed Dec. 10, 2010", 13 pgs.
"U.S. Appl. No. 11/422,423, Response filed Nov. 22, 2010 to Non Final Office Action maield Jul. 21, 2010", 11 pgs.
"U.S. Appl. No. 11/422,423, Response filed Jul. 8, 2010 to Final Office Action mailed Apr. 9, 2010", 9 pgs.
"U.S. Appl. No. 11/469,793 Non-Final Office Action mailed Sep. 30, 2010", 9 pgs.
"U.S. Appl. No. 11/469,793, Non-Final Office Action mailed Mar. 12, 2010", 6 pgs.
"U.S. Appl. No. 11/469,793, Response filed Jul. 12, 2010 to Non Final Office Action mailed Mar. 12, 2010", 10 pgs.
"U.S. Appl. No. 12/430,211 Non-Final Office Action mailed Sep. 1, 2010", 11 pgs.
"European Application No. 07797264.1, Office Action Mailed Jan. 20, 2010", 3 pgs.
"European Application No. 07797264.1, Response filed Apr. 28, 2010 to Office Action Mailed Jan. 20, 2010", 13 pgs.
"European Application Serial No. 07782375.5, Response filed Feb. 15, 2010 to Communication mailed Aug. 10, 2008", 8 pgs.
"European Application Serial No. 07782375.5, Office Action mailed Nov. 22, 2010", 5 Pgs.
"European Application Serial No. 07797400.4, European Office Action mailed Aug. 13, 2010", 4 Pgs.
Yimtae, K., et al., "Connection between the inner ear and the lymphatic system", Laryngoscope, 111(9), (Sep. 2001), 1631-5.
"European Application Serial No. 07782375.5, Response filed May 11, 2011 to Office Action mailed Nov. 22, 2010", 6 pgs.
"U.S. Appl. No. 11/422,423, Decision on Pre-Appeal Brief Request mailed May 24, 2011", 2 pgs.
"U.S. Appl. No. 11/422,423, Notice of Allowance mailed Jul. 6, 2011", 9 pgs.
"U.S. Appl. No. 11/422,423, Notice of Allowance mailed Oct. 18, 2011", 5 pgs.
"U.S. Appl. No. 11/422,423,Pre-Appeal Brief Request filed Apr. 11, 2011", 5 pgs.
"U.S. Appl. No. 11/469,793, Response filed Jul. 14, 2011 to Final Office Action mailed Mar. 14, 2011", 7 pgs.
"U.S. Appl. No. 11/752,377, Response filed Mar. 5, 2012 to Final Office Action mailed Oct. 4, 2011", 6 pgs.
"U.S. Appl. No. 11/752,377, Final Office Action mailed Oct. 4, 2011", 8 pgs.
"U.S. Appl. No. 11/752,377, Non Final Office Action mailed Mar. 30, 2012", 9 pgs.
"U.S. Appl. No. 11/752,377, Response filed Jul. 25, 2011 to Non Final Office Action mailed Mar. 23, 2011", 6 pgs.
"U.S. Appl. No. 12/430,2011, Non Final Office Action mailed Jun. 23, 2011", 16 pgs.
"U.S. Appl. No. 12/430,211, Final Office Action mailed Dec. 9, 2011", 7 pgs.
"U.S. Appl. No. 12/430,211, Response filed Oct. 21, 2011 to Non Final Office Action mailed Jun. 23, 2011", 8 pgs.
"U.S. Appl. No. 12/775,223, Non Final Office Action mailed Apr. 23, 2012", 11 pgs.
"Australian Application Serial No. 2007293445, First Examiners Report mailed Apr. 11, 2012", 1 pg.
"Japanese Application Serial No. 2009-514438, Office Action mailed Feb. 27, 2012", (w/English Translation), 5 pgs.
"Japanese Application Serial No. 2009-514438, Response filed May 25, 2012 to Office Action mailed Feb. 27, 2012", English Claims with response, 10 pgs.
"Japanese Application Serial No. 2009-514441, Office Action mailed Feb. 29, 2012", w/English Translation, 6 pgs.

* cited by examiner

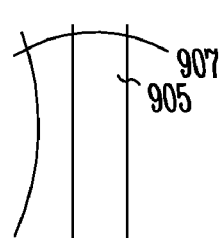 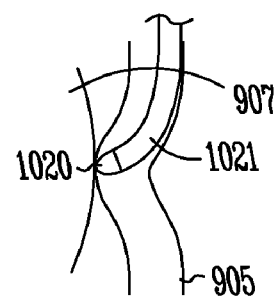
Fig. 9  Fig. 10
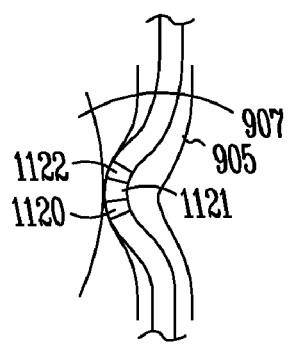 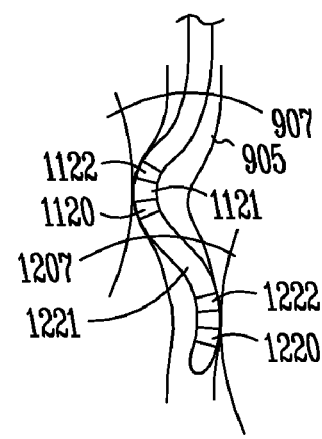
Fig. 11  Fig. 12
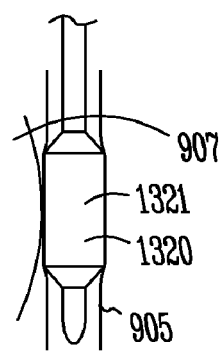
Fig. 13

METHOD AND APPARATUS FOR NEURAL STIMULATION VIA THE LYMPHATIC SYSTEM

CROSS REFERENCE TO RELATED APPLICATION

This application is a divisional of U.S. application Ser. No. 11/422,421, filed Jun. 6, 2006, now abandoned, which is hereby incorporated by reference in its entirety.

This application is related to co-pending, commonly assigned, U.S. patent application Ser. No. 11/422,423, entitled "METHOD AND APPARATUS FOR LYMPHATIC SYSTEM PACING AND SENSING," filed on Jun. 6, 2006, U.S. patent application Ser. No. 11/422,418, entitled "METHOD AND APPARATUS FOR GASTROINTESTINAL STIMULATION VIA THE LYMPHATIC SYSTEM," filed on Jun. 6, 2006, now U.S. Pat. No. 7,734,341, U.S. patent application Ser. No. 11/422,417, entitled "METHOD AND DEVICE FOR LYMPHATIC SYSTEM MONITORING," filed on Jun. 6, 2006, now issued as U.S. Pat. No. 7,526,337, and U.S. patent application Ser. No. 11/422,414, entitled "METHOD AND DEVICE FOR ENDO-LYMPHATIC STIMULATION," filed on Jun. 6, 2006, which are hereby incorporated herein by reference in their entirety.

TECHNICAL FIELD

This document relates generally to medical devices and particularly to an implantable system that delivers neural stimulation via one or more lymphatic vessels.

BACKGROUND

Neural stimulation has been applied to treat various pathological conditions. Controlled delivery of electrical stimulation pulses to a nerve generates, modulates, or inhibits activities of that nerve, thereby restoring the functions of that nerve and/or regulating the functions of the tissue or organ innervated by that nerve. One specific example of neural stimulation is to regulate cardiac functions and hemodynamic performance by delivering electrical stimulation pulses to portions of the autonomic nervous system. The heart is innervated with sympathetic and parasympathetic nerves. Activities in these nerves, including artificially applied electrical stimuli, modulate cardiac functions and hemodynamic performance. Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, has been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

Implantable medical systems are used to deliver neural stimulation. A typical implantable neural stimulation system includes an implantable neural stimulator that delivers electrical stimulation pulses through a plurality of stimulation electrodes. Depending on the location of the nerve to be stimulated, the stimulation electrodes may be incorporated onto the implantable neural stimulator and/or connected to the implantable neural stimulator using one or more implantable leads. In practice, the desirable stimulation sites may not be in a location with anatomical structure allowing for easy implantation of the implantable neural stimulator or easy access by the lead(s). The degree of risk associated with the implantation procedure increases with the degree of invasiveness. Therefore, given a desirable stimulation site, there is a need to minimize the invasiveness of implanting a system that delivers neural stimulation pulses to that stimulation site.

SUMMARY

An implantable neural stimulation system includes an implantable medical device having a neural stimulation circuit and at least one implantable lead configured to allow one or more stimulation electrodes to be placed in one or more lymphatic vessels of a patient, such as the patient's thoracic duct and/or vessels branching from the thoracic duct. Neural stimulation pulses are delivered from the implantable medical device to one or more target regions adjacent to the thoracic duct or the vessels branching from the thoracic duct through the one or more stimulation electrodes.

In one embodiment, a neural stimulation system includes an electrode assembly and an implantable medical device. The electrode assembly includes an electrode base configured to be implanted into a lymphatic vessel and a stimulation electrode on the electrode base. The electrode base is configured to cause a portion of the lymphatic vessel to substantially alter its natural path to contact a target region to which neural stimulation pulses are delivered and maintain the contact between the portion of the lymphatic vessel and the target region after the implantation of the electrode assembly. The implantable medical device includes a neural stimulation circuit that delivers the neural stimulation pulses through the stimulation electrode.

In one embodiment, a method for delivering neural stimulation is provided. Neural stimulation pulses are delivered from an implantable medical device to at least one stimulation electrode placed in a lymphatic vessel.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 9 is an illustration of a lymphatic vessel and a target region for neural stimulation.

FIG. 10 is an illustration of an embodiment of an electrode assembly for placement in the lymphatic vessel to allow for the neural stimulation.

FIG. 11 is an illustration of an embodiment of another electrode assembly for placement in the lymphatic vessel to allow for the neural stimulation.

FIG. 12 is an illustration of an embodiment of another electrode assembly for placement in the lymphatic vessel to allow for the neural stimulation.

FIG. 13 is an illustration of an embodiment of another electrode assembly for placement in the lymphatic vessel to allow for the neural stimulation.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses an implantable neural stimulation system including an implantable medical device delivering neural stimulation through at least one stimulation delivery device placed in a lymphatic vessel, such as the thoracic duct, of a patient. In one embodiment, the implantable neural stimulation system includes a transluminal lead configured for insertion into a portion of the lymphatic vessel to allow one or more stimulation electrodes to be placed in the lymphatic vessel. The implantable medical device includes a neural stimulation circuit that generates electrical pulses. The electrical pulses are delivered to one or more target regions adjacent to the lymphatic vessel through the one or more stimulation electrodes placed in the lymphatic vessel. While the thoracic duct is specifically discussed in this document as an example of such a lymphatic vessel, neural stimulation pulses are delivered through any one or more lymphatic vessels, including, but not limited to, the thoracic duct, lymphatic vessels branching from the thoracic duct, the right lymphatic duct, and lymphatic vessels branching from the right lymphatic duct.

While electrical stimulation is specifically discussed in this document as an example, the present subject matter includes neurostimulation using any form of energy that is capable of stimulating one or more components of the nervous system via the lymphatic vessel such as the thoracic duct. In various embodiments, the stimulation delivery device placed in the lymphatic vessel generates or receives neural stimuli, which are then delivered to one or more neural stimulation sites via the lymphatic vessel. The neural stimuli are in one or more forms of energy that are capable of eliciting a neural response, such as electrical, magnetic, electromagnetic, thermal, and/or acoustic (including ultrasonic) energy.

Figure 1:
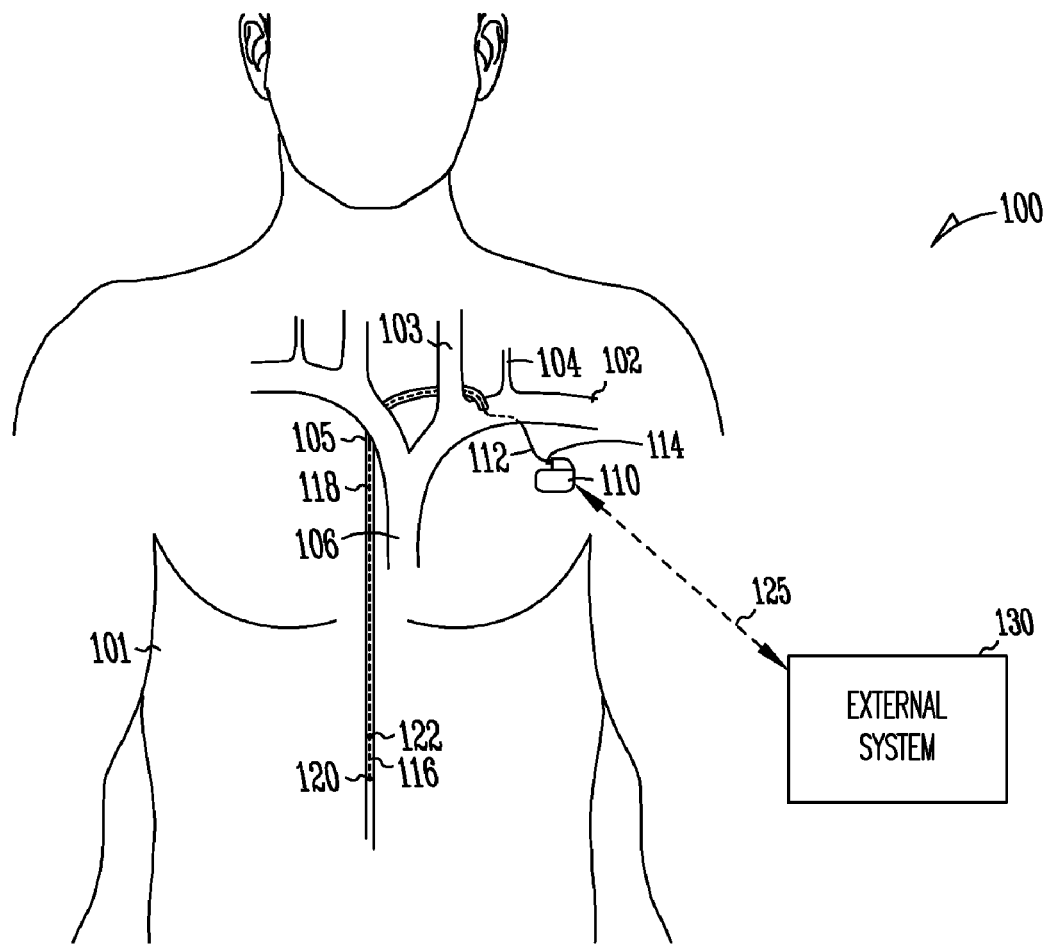
FIG. 1 is an illustration of an embodiment of a neural stimulation system and portions of an environment in which the neural stimulation system is used.

FIG. 1 is an illustration of an embodiment of a neural stimulation system 100 and portions of an environment in which system 100 is used. System 100 includes an implantable medical device 110, a lead 112, an external system 130, and a telemetry link 125 providing for communication between implantable medical device 110 and external system 130.

System 100 delivers neural stimulation pulses through at least one electrode placed in a thoracic duct 105, which is part of the lymphatic system of a patient's body 101. The lymphatic system includes lymph tissue, nodes, and vessels. Interstitial fluid is absorbed from tissue, filtered through lymph nodes, and empties into lymphatic vessels. FIG. 1 illustrates portions of thoracic duct 105, a subclavian vein 102, a left external jugular vein 104, a left internal jugular vein 103, and a superior vena cava 106. Thoracic duct 105 connects to the venous system at the juncture of subclavian vein 102 and a left internal jugular vein 103. The fluid (lymph) from the lower body flows up to thoracic duct 105 and empties into subclavian vein 102 from thoracic duct 105. Thoracic duct 105 is located in the posterior mediastinal area of body 101, adjacent to the heart and various portions of the nervous system including portions of the vagus, sympathetic, and phrenic nerves. Electrical stimulation of such nerves is delivered by using one or more stimulation electrodes placed within thoracic duct 105. Thoracic duct 105 is used as a conduit for advancing the one or more stimulation electrodes to a location from which electrical stimulation can be delivered to a target region of the nervous system of body 101. This approach to the process of electrode placement for neural stimulation has the potential of reducing the invasiveness of implantation procedure under many circumstances.

Implantable medical device 110 generates neural stimulation pulses that are electrical pulses and delivers the neural stimulation pulses through lead 112. In one embodiment, implantable medical device 110 also senses neural activities using at least lead 112. In various embodiments, implantable medical device 110 is capable of sensing other physiological signals and/or delivering therapies in addition to the neural stimulation. Examples of such additional therapies include cardiac pacing therapy, cardioversion/defibrillation therapy, cardiac resynchronization therapy (CRT), cardiac remodeling control therapy (RCT), drug therapy, cell therapy, and gene therapy. In various embodiments, implantable medical device 110 delivers the neural stimulation in coordination with one or more such additional therapies. In one embodiment, in addition to lead 112, system 100 includes one or more endocardial and/or epicardial leads for delivering pacing and/or defibrillation pulses to the heart.

Lead 112 is an implantable neural stimulation lead including a proximal end 114, a distal end 116, and an elongate lead body 118 between proximal end 114 and distal end 116. Proximal end 114 is coupled to implantable medical device 110. Distal end 116 includes at least one stimulation electrode for delivering the neural stimulation pulses to a target region of the nervous system of body 101. In one embodiment, as illustrated in FIG. 1, distal end 116 includes stimulation electrodes 120 and 122. In various other embodiments, distal end 116 includes one stimulation electrode or three or more stimulation electrodes. In one embodiment, a reference electrode is incorporated onto implantable medical device 110. In a specific embodiment, implantable medical device 110 includes a hermetically sealed conductive housing that functions as the reference electrode. Neural stimulation pulses are delivered using (i) two stimulation electrodes in distal end 116 (electrodes 120 or 122), or (ii) a stimulation electrode (electrode 120 or 122) in distal end 116 and the reference electrode on implantable medical device 110. In various embodiments, one or more of the stimulation electrodes are also used for sensing one or more neural signals. The distal portion of elongate lead body 118 (a substantial portion of elongate lead body 118 coupled to distal end 116) is configured for placement in subclavian vein 102 and thoracic duct 105, such that distal end 116 is placed in thoracic duct 105. During the implantation of lead 112, distal end 116 is inserted into subclavian vein 102 through an incision, advanced in subclavian vein 102 toward thoracic duct 105, inserted into thoracic duct 105 from subclavian vein 102, and advanced in thoracic duct 105 until a predetermined location in thoracic duct 105 is reached. In one embodiment, the position of distal end 116 is adjusted by delivering test neural stimulation pulses and detecting evoked neural signals and/or other physiological responses. In one embodiment, lead 112 includes a fixation mechanism configured to stabilize distal end 116 in the determined position in thoracic duct 105. Implantable medical device 110 is connected to proximal end 114 and is subcutaneously implanted. One example of method and apparatus for accessing the lymphatic system is discussed in U.S. patent application Ser. No. 11/422,423, entitled "METHOD AND APPARATUS FOR LYMPHATIC SYSTEM PACING AND SENSING," filed on Jun. 6, 2006, assigned to Cardiac Pacemakers, Inc., which is incorporated herein by reference in its entirety. Specific examples of electrode configurations and placement are also discussed in detail below, with reference to FIGS. 9-12.

In one embodiment, lead 112 is configured such that distal end 116 can be further advanced into a lymphatic vessel branching from thoracic duct 105, such as the gastric branch, so that the stimulation electrode can be placed in close proximity of a desirable target region. After the distal end 116 is inserted into thoracic duct 105, it is advanced to the junction of thoracic duct 105 and the branching lymphatic vessel and inserted to the branching lymphatic vessel. While the placement of at least one stimulation electrode in the thoracic duct is specifically discussed as an example of providing for access to a target region, the present subject matter generally includes introducing one or more stimulus delivery devices such as one or more stimulation electrodes to a stimulation site via a lymphatic vessel. In various embodiments, neural stimulation pulses are delivered through one or more stimulation electrodes placed in the lymphatic vessel and/or one or more stimulation electrodes placed in a structure that is accessible through the lymphatic vessel, including another lymphatic vessel branching from the lymphatic vessel.

In one embodiment, system 100 includes two or more leads each including one or more stimulation electrodes arranged to be placed in thoracic duct 105. In another embodiment, a lead includes a plurality of electrodes arranged for delivering independently controllable neural stimulation pulses to two or more target regions.

External system 130 communicates with implantable medical device 110 and provides for access to implantable medical device 110 by a physician or other caregiver. In one embodiment, external system 130 includes a programmer. In another embodiment, external system 130 is a patient management system including an external device communicating with implantable medical device 110 via telemetry link 125, a remote device in a relatively distant location, and a telecommunication network linking the external device and the remote device. The patient management system allows access to implantable medical device 110 from a remote location, for purposes such as monitoring patient status and adjusting therapies. In one embodiment, telemetry link 125 is an inductive telemetry link. In another embodiment, telemetry link 125 is a far-field radio-frequency (RF) telemetry link. Telemetry link 125 provides for data transmission from implantable medical device 110 to external system 130. This includes, for example, transmitting real-time physiological data acquired by implantable medical device 110, extracting physiological data acquired by and stored in implantable medical device 110, extracting patient history data such as occurrences of predetermined types of pathological events and therapy deliveries recorded in implantable medical device 110, and/or extracting data indicating an operational status of implantable medical device 110 (e.g., battery status and lead impedance). Telemetry link 125 also provides for data transmission from external system 130 to implantable medical device 110. This includes, for example, programming implantable medical device 110 to acquire physiological data, programming implantable medical device 110 to perform at least one self-diagnostic test (such as for a device operational status), and/or programming implantable medical device 110 to deliver one or more therapies and/or to adjust the delivery of one or more therapies.

Figure 2:
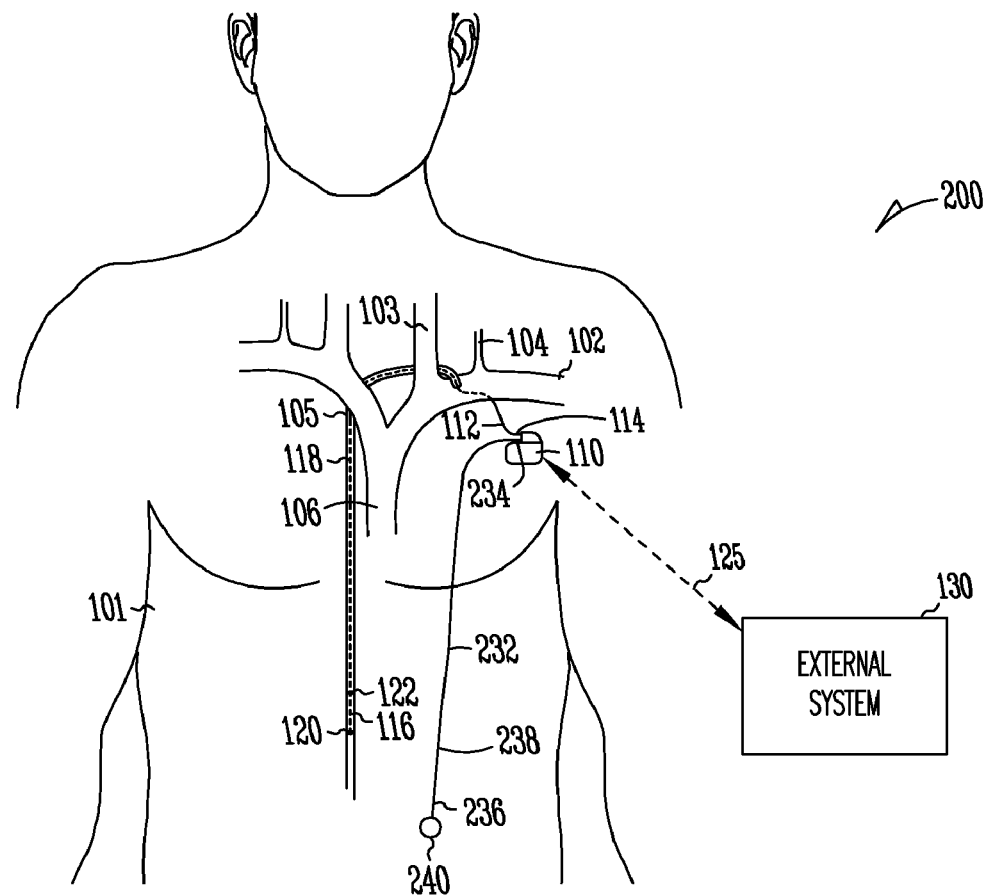
FIG. 2 is an illustration of another embodiment of the neural stimulation system and portions of the environment in which the neural stimulation system is used.

FIG. 2 is an illustration of an embodiment of a neural stimulation system 200 and portions of the environment in which system 200 is used. System 200 includes the components of neural stimulation system 100 and an additional lead. That is, neural stimulation system 200 includes implantable medical device 110, leads 112 and 232, external system 130, and telemetry link 125.

Lead 232 is an implantable neural stimulation lead including a proximal end 234, a distal end 236, and an elongate lead body 238 between proximal end 234 and distal end 236. Proximal end 234 is coupled to implantable medical device 110. Distal end 236 includes at least one electrode. In one embodiment, as illustrated in FIG. 2, lead 232 includes an electrode 240 at distal end 236. In another embodiment, lead 232 includes a plurality of stimulation electrodes. In one embodiment, lead 232 is configured for subcutaneous placement, external to thoracic duct 105. In one embodiment, electrode 240 is used as a reference electrode.

Lead 232 expands the range of target regions to which neural stimulation pulses can be delivered from implantable medical device 110. In various embodiments, neural stimulation pulses are delivered through any pair of electrodes of system 200 including (i) two stimulation electrodes in distal end 116 (electrodes 120 and 122), (ii) a stimulation electrode in distal end 116 (electrode 120 or 122) and electrode 240 (as the reference electrode), or (iii) a stimulation electrode in distal end 116 (electrode 120 or 122) and the reference electrode on implantable medical device 110. In one embodiment, distal ends 116 and 236 are positioned such as a target structure for the neural stimulation is approximately between a stimulation electrode in distal end 116 (electrode 120 or 122) and a reference electrode (electrode 240 or the reference electrode on implantable medical device 110). For example, the target structure is a portion of the spinal cord of body 101.

Figure 3:
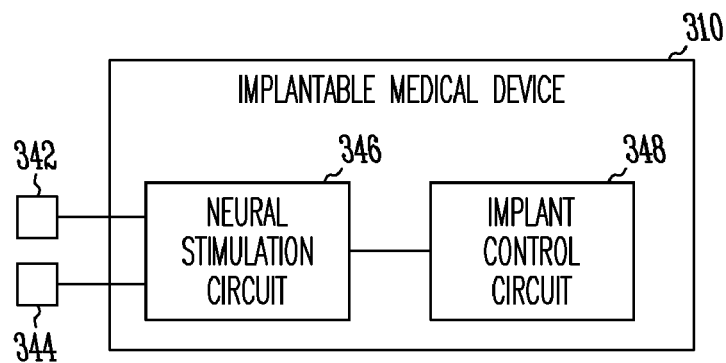
FIG. 3 is a block diagram illustrating an embodiment of an implantable medical device of the neural stimulation system.

FIG. 3 is a block diagram illustrating an embodiment of an implantable medical device 310, which is a specific embodiment of implantable medical device 110. Implantable medical device 310 includes a neural stimulation circuit 346 and an implant control circuit 348. Neural stimulation circuit 346 delivers neural stimulation pulses to a pair of stimulation electrodes 342 and 344, through which the neural stimulation pulses are delivered to a target region in the nervous system. At least one of stimulation electrodes 342 and 344 is placed in thoracic duct 105. Implant control circuit 348 controls the delivery of the neural stimulation pulses from neural stimulation circuit 346.

In one embodiment, stimulation electrodes 342 and 344 are both in thoracic duct 105 and adjacent to the target region, such as electrodes 120 and 122. In another embodiment, stimulation electrode 342 is in thoracic duct 105 and adjacent to the target region, such as electrode 120 or 122, and stimulation electrode 344 is external to thoracic duct 105, such as electrode 240 or a reference electrode on implantable medical device 310. In one embodiment, the target region is approximately between stimulation electrodes 342 and 344.

In various embodiments, the target region includes one or more components of the nervous system that are adjacent to the thoracic duct in the posterior mediastinal region or abdominal region. Examples of the target region include the sympathetic nerves, the parasympathetic nerves (including the vagus nerve), the phrenic nerve, the spinal cord, the brain stem, the renal nerves, and the baroreceptors in the carotid artery and aorta. In one embodiment, cardiac functions are regulated by applying neural stimulation including one or more of sympathetic excitation, sympathetic inhibition, parasympathetic excitation, and parasympathetic inhibition. One example of a system capable of providing excitatory stimulation and inhibitory stimulation to both sympathetic nerves and parasympathetic nerves is discussed in U.S. patent application Ser. No. 11/124,791, entitled "METHOD AND APPARATUS FOR CONTROLLING AUTONOMIC BALANCE USING NEURAL STIMULATION," filed on May 9, 2005, assigned to Cardiac Pacemakers, Inc., which is incorporated herein by reference in its entirety.

For illustration purposes, FIG. 3 shows the pair of stimulation electrodes 342 and 344. In various embodiments, neural stimulation circuit 346 delivers neural stimulation pulses through one or more pairs of stimulation electrodes selected from a plurality of stimulation electrodes. In one embodiment, neural stimulation circuit 346 includes two or more stimulation output channels each delivering neural stimulation pulses through a pair of stimulation electrodes. In another embodiment, an electrode array with a plurality of stimulation electrodes is placed in the thoracic duct, and one or more stimulation electrodes are selected for delivering neural stimulation pulses by testing the physiological effect of stimulation associated with each stimulation electrode.

Figure 4:
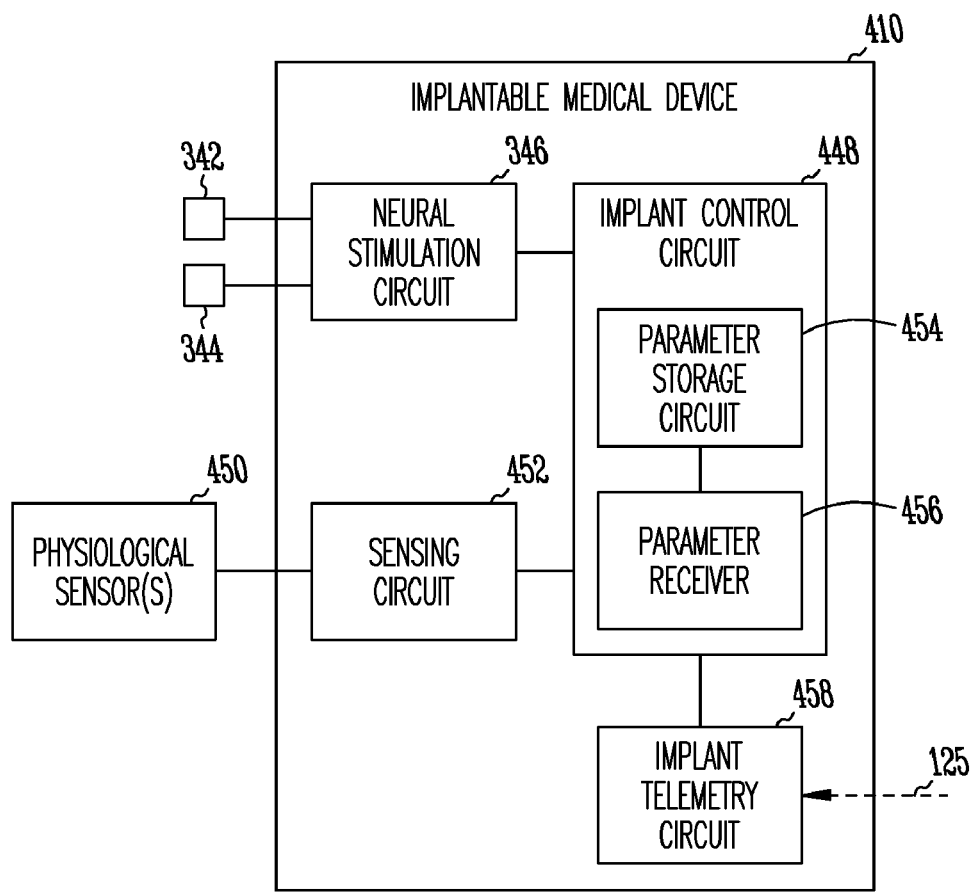
FIG. 4 is a block diagram illustrating a specific embodiment of the implantable medical device.

FIG. 4 is a block diagram illustrating an embodiment of an implantable medical device 410, which is another specific embodiment of implantable medical device 110. Implantable medical device 410 includes neural stimulation circuit 346, a sensing circuit 452, an implant control circuit 448, and an implant telemetry circuit 458. One or more physiological sensors 450 are housed within implantable medical device 410, incorporated onto implantable medical device 410, and/or connected to implantable medical device 410 using a lead.

Physiological sensor(s) 450 sense one or more physiological signals indicative of neural function and/or physiological functions regulated by the components of the nervous system to be stimulated. Sensing circuit 452 processes the one or more physiological signals and produces signals indicative of a need to start, stop, or adjust the neural stimulation. Examples of such physiological signals include signals indicative of heart rate, heart rate variability (HRV), and blood pressure. In one embodiment, physiological sensor(s) 450 include one or both of stimulation electrodes 342 and 344, which are utilized as sensing electrodes.

Implant control circuit 448 is a specific embodiment of implant control circuit 348 and controls the delivery of the neural stimulation pulses from neural stimulation circuit 346 using a plurality of stimulation parameters. Implant control circuit 448 includes a parameter storage circuit 454 and a parameter receiver 456. Parameter storage circuit 454 stores values of the plurality of stimulation parameters. Examples of such stimulation parameters include pulse amplitude, pulse width, and pulse frequency (or inter-pulse interval). The values of the plurality of stimulation parameters are adjustable. Parameter receiver 456 receives values of the plurality of stimulation parameters and updates parameter storage circuit 454 with the received values. In one embodiment, implant control circuit 448 controls the delivery of the neural stimulation pulses from neural stimulation circuit 346 using one or more physiological signals sensed by physiological sensor(s) 450. In various embodiments, each sensed physiological signal is used as one or more of a triggering signal to start or stop the neural stimulation, a safety assurance signal to start, stop, or adjust the intensity of the neural stimulation, and a feedback signal to provide closed-loop neural stimulation.

Implant telemetry circuit 458 transmits and receives data via telemetry link 125. In one embodiment, the values of the plurality of stimulation parameters are externally programmable, and the programmed values are received from external system 130 through telemetry link 125.

Figure 5:
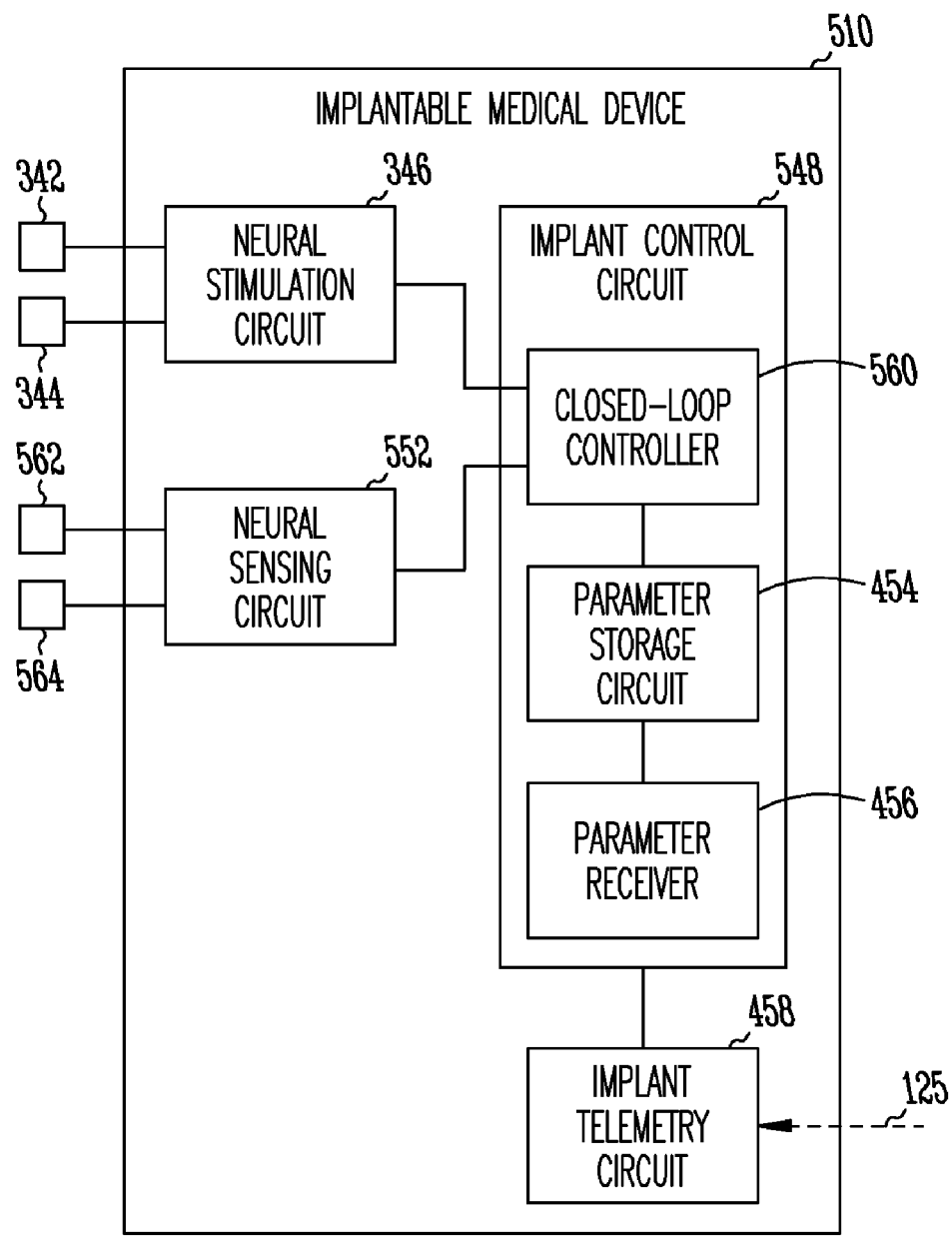
FIG. 5 is a block diagram illustrating another specific embodiment of the implantable medical device.

FIG. 5 is a block diagram illustrating an implantable medical device 510, which is a specific embodiment of implantable medical device 410. Implantable medical device 510 includes neural stimulation circuit 346, a neural sensing circuit 552, an implant control circuit 548, and implant telemetry circuit 458.

Neural sensing circuit 552 is a specific embodiment of sensing circuit 452 and processes a neural signal sensed using neural sensing electrodes 562 and 564, which represent a specific embodiment of physiological sensor(s) 450. In one embodiment, neural sensing circuit 552 processes two or more neural signals sensed using additional neural sensing electrodes. In one embodiment, the neural signal is sensed from the same site to which the neural stimulation pulses are delivered, and stimulation electrodes 342 and 344 are used as neural sensing electrodes 562 and 564. In other words, stimulation electrodes 342 and 344 and neural sensing electrodes 562 and 564 are physically the same pair of electrodes. In another embodiment, the neural signal is sensed from a site different from the site to which the neural stimulation pulses are delivered. At least one of stimulation electrodes 342 and 344 is not used as any of neural sensing electrodes 562 and 564.

Implant control circuit 548 is a specific embodiment of implant control circuit 448 and includes a closed-loop controller 560, parameter storage circuit 454, and parameter receiver 456. Implant control circuit 548 controls the delivery of the neural stimulation pulses from neural stimulation circuit 346 using a plurality of stimulation parameters and the sensed and processed neural signal. Closed-loop controller 560 controls the delivery of the neural stimulation pulses using the sensed and processed neural signal as an input for feedback control. Examples of closed-loop neural stimulation are discussed in U.S. patent application Ser. No. 11/280,940, entitled "SYSTEM AND METHOD FOR CLOSED-LOOP NEURAL STIMULATION," filed on Nov. 16, 2005, assigned to Cardiac Pacemakers, Inc., which is incorporated herein by reference in its entirety.

Figure 6:
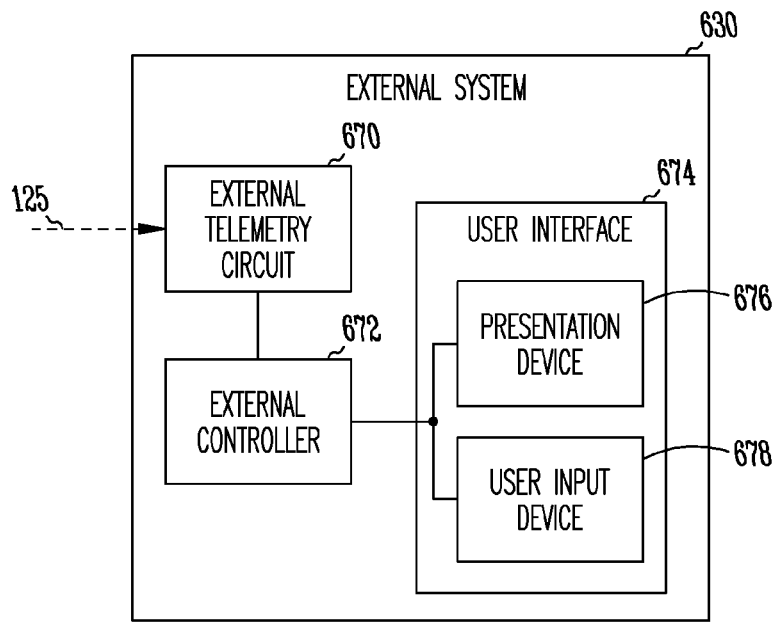
FIG. 6 is a block diagram illustrating an embodiment of an external system of the neural stimulation system.

FIG. 6 is a block diagram illustrating an embodiment of an external system 630, which is a specific embodiment of external system 130. External system 630 includes an external telemetry circuit 670, an external controller 672, and a user interface 674. External telemetry circuit 670 transmits and receives data via telemetry link 125. External controller 672 controls the operation of external system 630. User interface 674 allows a user such as a physician or other caregiver to communicate with implantable medical device 110 through external system 630. User interface 674 includes a presentation device 676 and a user input device 678. User input device 678 allows for the programming of the values of the plurality of stimulation parameters. In one embodiment, presentation device 676 and user input device 678 are integrated or partially integrated to include an interactive screen allowing for programming of implantable medical device 110.

In one embodiment, external system 630 includes a programmer. In another embodiment, external system 630 includes a patient management system as discussed below with reference to FIG. 7.

Figure 7:
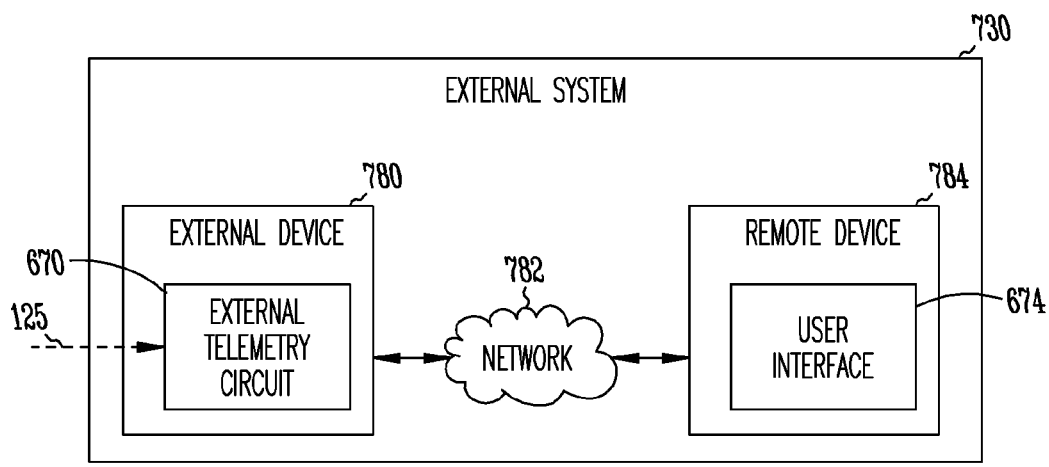
FIG. 7 is a block diagram illustrating an embodiment of the external system being a patient management system.

FIG. 7 a block diagram illustrating an embodiment of an external system 730, which is a specific embodiment of external system 630. As illustrated in FIG. 7, external system 730 is a patient management system including an external device 780, a telecommunication network 782, and a remote device 784. External device 780 is placed within the vicinity of implantable medical device 110 and includes external telemetry system 670 to communicate with the implantable medical device via telemetry link 125. Remote device 784 is in a remote location and communicates with external device 780 through network 782. Remote device 784 includes user interface 674 to allow the physician or other caregiver to monitor and treat a patient from a distant location and/or allowing access to various treatment resources from the remote location.

Figure 8:
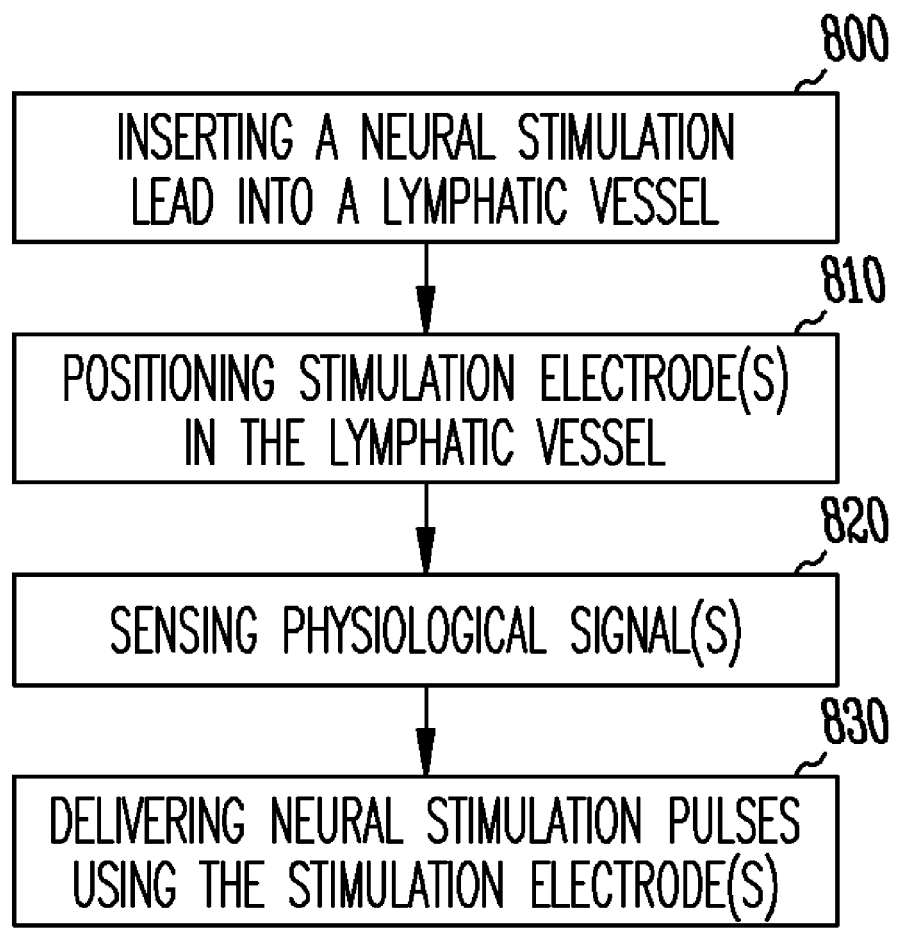
FIG. 8 is a flow chart illustrating a method for delivering neural stimulation via the thoracic duct.

FIG. 8 is a flow chart illustrating a method for delivering neural stimulation via the thoracic duct. In one embodiment, the method is performed using system 100 or system 200, including the various embodiments of their components discussed above.

A neural stimulation lead is inserted into a lymphatic vessel of a patient at 800. In one embodiment, this lymphatic vessel is the thoracic duct. The neural stimulation lead is an implantable transluminal lead having a proximal end configured for connection to an implantable medical device and a distal end including one or more stimulation electrodes. To insert the neural stimulation lead into the thoracic duct such that neural stimulation pulses can be delivered through the stimulation electrode(s), an opening is made on the subclavian vein, upstream from the junction of the subclavian vein and the ostium of the thoracic duct. The distal end of the neural stimulation lead is inserted into the subclavian vein through the opening and advanced toward the junction of the subclavian vein and the ostium of the thoracic duct downstream. Then, the neural stimulation lead is guided into the thoracic duct and advanced in the thoracic duct until the distal end reaches a region determined by the target to which the neural stimulation pulses are delivered. Examples of the target region include any nerve of other components of the nervous system in the mediastinal or abdominal region, adjacent to the thoracic duct, such as sympathetic nerves, parasympathetic nerves including the vagus nerve, the phrenic nerve, renal nerves, the spinal cord, the brain stem, and baroreceptors in the carotid artery and aorta. In one embodiment, to further approach a desirable target region, the distal end of the neural stimulation lead is guided into a lymphatic vessel branching from the thoracic duct.

The stimulation electrode(s) of the neural stimulation lead are positioned in the lymphatic vessel, such as the thoracic duct or the lymphatic vessel branching from the thoracic duct, at 810. In one embodiment, after the distal end of the neural stimulation lead reaches the region determined by the target, test neural stimulation pulses are delivered. The distal end is moved in the thoracic duct or the lymphatic vessel branching from the thoracic duct until it reaches a position identified by detecting satisfactory responses to the stimulation, such as evoked neural signals and/or other anticipated physiological effects. The distal end with the stimulation electrode(s) is then stabilized in that position. In another embodiment, the neural stimulation lead includes a plurality of stimulation electrodes. After the neural stimulation lead is inserted, test neural stimulation pulses are delivered to different stimulation electrodes or different combinations of the stimulation electrodes, one at a time. A stimulation electrode or a combination of stimulation electrodes is identified for an intended therapy based on the responses to the stimulation, such as evoked neural signals and/or other anticipated physiological effects.

One or more physiological signals are sensed at 820. In one embodiment, at least one physiological signal is sensed to indicate a need to start, stop, or adjust the delivery of the neural stimulation. In another embodiment, at least one physiological signal is sensed for monitoring, diagnostic, and/or therapeutic purposes other then the neural stimulation. In one embodiment, one or more neural signals are sensed. In a specific embodiment, a neural signal is sensed from the nerve to which the neural stimulation is delivered. In another embodiment, one or more signals each indicative of a physiological function regulated by the stimulated nerve are sensed.

Neural stimulation pulses are delivered using the stimulation electrode(s) positioned in the lymphatic vessel, such as the thoracic duct or the lymphatic vessel branching from the thoracic duct, at 830. In one embodiment, the neural stimulation pulses are delivered through two stimulation electrodes positioned in the thoracic duct or the lymphatic vessel branching from the thoracic duct. In another embodiment, the neural stimulation pulses are delivered using a stimulation electrode positioned in the thoracic duct or the lymphatic vessel branching from the thoracic duct and another stimulation electrode positioned in a location in the body external to the lymphatic vessels. In a specific embodiment, the neural stimulation pulses are delivered to a portion of the nervous system approximately between a pair of stimulation electrodes. The delivery of the neural stimulation pulses is controlled using a plurality of stimulation parameters. Examples of the stimulation parameters include pulse amplitude, pulse width, and pulse frequency (or inter-pulse interval). These stimulation parameters are adjustable. In one embodiment, a user such as a physician or other caregiver programs one or more values of the plurality of stimulation parameters. In one embodiment, the delivery of the neural stimulation pulses are also controlled using the one or more physiological signals, including the one or more neural signals.

The neural stimulation pulses are delivered via the thoracic duct or the lymphatic vessel branching from the thoracic duct to treat one or more clinical conditions each associated with a physiological function regulated by a nerve or other component of the nervous system that is adjacent the thoracic duct or the lymphatic vessel branching from the thoracic duct. Examples of such clinical conditions include respiratory disorders, abnormal blood pressure, cardiac arrhythmias, myocardial infarction or ischemic insult (angina), heart failure, epilepsy, depression, renal disorders, pain, migraine, obesity, movement disorders, and incontinence. Specific examples of the treatment include (i) treatment of hypertension by baroreceptor stimulation, (ii) treatment of heart failure by sympathetic inhibition or vagal excitation; (iii) control of post-myocardial infarction remodeling by sympathetic inhibition or vagal excitation, (iv) mitigation of chronic pain by neural activation or blocking, (v) treatment of vascular pain including refractory angina and peripheral vascular diseases (PVD) by spinal cord stimulation, (vi) treatment of rachidian pain including failed back surgery syndrome (FBSS), degenerative low back leg pain (LBLP), nerve root lesions, incomplete spine lesions and spinal stenosis by spinal cord stimulation, (vii) treatment of type 1 or type 2 chronic regional pain syndrome (CRPS) by spinal cord stimulation, and (viii) treatment of perineal pain and urological diseases by spinal cord stimulation, and restoration of lower extremity motor functions such as standing and walking after spinal cord injury by ventral spinal cord stimulation.

FIGS. 9-13 illustrate, by way of example, various embodiments of an electrode assembly for placement in the lymphatic vessel to allow for the neural stimulation. The electrode assembly includes one or more electrode bases. One or more stimulation electrodes are incorporated onto and/or integrated with each of the one or more electrode bases. In one embodiment, the one or more electrode bases each are formed as portion of a lead such as lead 112. In one specific embodiment, an electrode base is formed at distal end 116 of lead 112, and stimulation electrodes 120 and 122 are on that electrode base. In another specific embodiment, one or more electrode bases are formed in elongate lead body 118 of lead 112. In another embodiment, electrode bases are formed at distal end 116 and elongate lead body 118 of lead 112 to provide for delivery of the neural stimulation pulses to multiple target regions.

FIG. 9 is an illustration of a lymphatic vessel 905 and a target region 907 in their natural state. Target region 907 is a region in the nervous system to which the neural stimulation pulses are delivered. As illustrated in FIG. 9, lymphatic vessel 905 and target region 907 are not in direct contact, or not constantly in direct contact, with each other in their natural state. Electrode assemblies illustrated in FIGS. 10-13 each cause and maintain a substantially constant and direct contact between lymphatic vessel 905 and target region 907 by substantially altering the natural path of lymphatic vessel 905. Such a substantially constant and direct contact allows for a reliable delivery of neural stimulation pulses from one or more electrodes in lymphatic vessel 905 to target region 907. In various embodiments, lymphatic vessel 905 represents one of the thoracic duct, a vessel branching from the thoracic duct, or any lymphatic vessel suitable for placement of the one or more electrodes for the delivery of the neural stimulation pulses.

FIG. 10 is an illustration of an embodiment of an electrode assembly including an electrode base 1021 configured to be implanted in lymphatic vessel 905 and a stimulation electrode 1020 on electrode base 1021. Electrode base 1021 has an elongate shape and includes a bias configured to cause a portion of lymphatic vessel 905 to substantially alter its natural path to contact target region 907. The bias also allows electrode 1020 to be in contact with the inner wall of lymphatic vessel 905 for delivering the neural stimulation pulses to target region 907. Electrode base 1021 has a stiffness allowing for stabilizing the position of stimulation electrode 1020 in lymphatic vessel 905 and maintaining the contact between the portion of lymphatic vessel 905 and target region 907 after implantation. In one embodiment, electrode base 1021 is in a helical form. In one embodiment, electrode base 1021 includes an elongate body having shape memory characteristics such that it returns to its preformed shape after the implantation procedure during which a stylet or guide wire may be used. The shape memory characteristics are provided by using a shape memory polymer such as polyether polyurethane or a shape memory metal. In one embodiment, the electrode assembly is coupled to implantable medical device 110 via a lead such as lead 112. In a specific embodiment, electrode base 1021 is formed at distal end 116 of lead 112, with stimulation electrode 1020 being stimulation electrode 120. In other specific embodiments, two or more stimulation electrodes are incorporated into electrode base 1021.

FIG. 11 is an illustration of an embodiment of another electrode assembly including an electrode base 1121 configured to be implanted in lymphatic vessel 905 and stimulation electrodes 1120 and 1122, both on electrode base 1121. Electrode base 1121 has an elongate shape and includes a bias configured to cause a portion of lymphatic vessel 905 to substantially alter its natural path to contact target region 907. The bias also allows electrodes 1120 and 1122 to be in contact with the inner wall of lymphatic vessel 905 for delivering the neural stimulation pulses to target region 907 using either or both of electrodes 1120 and 1122. Electrode base 1121 has the stiffness allowing for stabilizing the positions of stimulation electrodes 1120 and 1122 in lymphatic vessel 905 and maintaining the contact between the portion of lymphatic vessel 905 and target region 907 after implantation. In one embodiment, electrode base 1121 is in a helical form. In one embodiment, electrode base 1121 includes an elongate body having shape memory characteristics such that it returns to its preformed shape after the implantation procedure during which a stylet or guide wire may be used. The shape memory characteristics are provided by using a shape memory polymer such as polyether polyurethane or a shape memory metal. In one embodiment, the electrode assembly is coupled to implantable medical device 110 via a lead such as lead 112. In a specific embodiment, electrode base 1121 is formed at distal end 116 of lead 112, with stimulation electrodes 1120 and 1122 being stimulation electrodes 120 and 122. In other specific embodiments, one stimulation electrode, or three or more stimulation electrodes, are incorporated into electrode base 1121.

FIG. 12 is an illustration of an embodiment of another electrode assembly including an electrode base 1121 with stimulation electrodes 1120 and 1122 and another electrode base 1221 with stimulation electrodes 1220 and 1222. Electrode bases 1121 and 1221 are both configured to be implanted in lymphatic vessel 905. Electrode bases 1121 has the elongate shape and includes the bias configured to cause a portion of lymphatic vessel 905 to substantially alter its natural path to contact target region 907. The bias also allows electrodes 1120 and 1122 to be in contact with the inner wall of lymphatic vessel 905 for delivering neural stimulation pulses to target region 907 using either or both of electrodes 1120 and 1122. Electrode bases 1221 has an elongate shape and includes a bias configured to cause a portion of lymphatic vessel 905 to substantially alter its natural path to contact a target region 1207. The bias also allows electrodes 1220 and 1222 to be in contact with the inner wall of lymphatic vessel 905 for delivering neural stimulation pulses to target region 1207 using either or both of electrodes 1220 and 1222. Electrode bases 1121 and 1221 each have a stiffness allowing for stabilizing the positions of the stimulation electrodes in lymphatic vessel 905 and maintaining the contact between the portion of lymphatic vessel 905 and target region 907 after implantation. In one embodiment, electrode bases 1121 and 1221 are each in a helical form. In one embodiment, electrode bases 1121 and 1221 each include an elongate body having shape memory characteristics such that it returns to its preformed shape after the implantation procedure during which a stylet or guide wire may be used. The shape memory characteristics are provided by using a shape memory polymer such as polyether polyurethane or a shape memory metal. In one embodiment, the electrode assembly is coupled to implantable medical device 110 via a lead such as lead 112. In a specific embodiment, electrode base 1121 is formed at distal end 116 of lead 112, with stimulation electrodes 1120 and 1122 being stimulation electrodes 120 and 122, and electrode base 1221 is formed in elongate lead body 118 of lead 112. In other specific embodiments, one stimulation electrode, or three or more stimulation electrodes, are incorporated into each of electrode bases 1121 and 1221.

FIG. 13 is an illustration of an embodiment of another electrode assembly including an electrode base 1321 and a stimulation electrode 1320. Electrode base 1321 is expandable. After being expanded, electrode base 1321 causes a portion of lymphatic vessel 905 to substantially expand to contact target region 907. The expansion of electrode base 1321 also allows electrode 1320 to be in stable contact with the inner wall of lymphatic vessel 905 for delivering neural stimulation pulses to target region 907. In one embodiment, electrode base 1321 includes a stent that is expanded in the lymphatic vessel to maintain patency of the vessel. In one embodiment, stimulation electrode 1320 is incorporated into the stent. In another embodiment, the stent is made of metal and functions as stimulation electrode 1320. In another embodiment, stimulation electrode 1320 is integrated into the stent to be a portion of its structure. The stent also stabilizes the position of stimulation electrode 1320 in lymphatic vessel 905 and prevents obstruction of the lymphatic flow. In one embodiment, the electrode assembly is coupled to implantable medical device 110 via a lead such as lead 112. In a specific embodiment, the stent is incorporated into distal end 116 of lead 112. In another embodiment, the stent is incorporated into elongate lead body 118 of lead 112. In another embodiment, two or more stents are incorporated into elongate lead body 118 and/or distal end 116 of lead 112.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering neural stimulation to a body having a nervous system and lymphatic vessels including a thoracic duct and vessels branching from the thoracic duct, the method comprising:
   delivering neural stimulation pulses from an implantable medical device to a target region of the nervous system through at least a first stimulation electrode coupled to the implantable medical device and placed in a location in the thoracic duct or one of the vessels branching from the thoracic duct to treat one or more clinical conditions each associated with a physiological function regulated by the target region, wherein the location is adjacent to the target region, and the first stimulation electrode is advance to the location using the thoracic duct as a conduit to reduce invasiveness of a procedure for implantation of the first stimulation electrode;
   wherein the one or more clinical conditions is a respiratory disorder, abnormal blood pressure, cardiac arrhythmia, myocardial infarction, ischemic insult, heart failure, epilepsy, depression, renal disorders, pain, migraine, obesity, movement disorders, and incontinence.

2. The method of claim 1, further comprising altering a natural path of the one of the lymphatic vessels to cause a portion of the one of the lymphatic vessels to contact a target region to which the neural stimulation are delivered using an electrode base configured to be implanted in the one of the lymphatic vessels, and wherein the first stimulation electrode is incorporated into or integrated with the electrode base.

3. The method of claim 1, wherein delivering the neural stimulation pulses comprises delivering the neural stimulation pulses through at least the first stimulation electrode placed in the thoracic duct.

4. The method of claim 1, wherein delivering the neural stimulation pulses comprises delivering the neural stimulation pulses through at least the first stimulation electrode placed in the one of the vessels branching from the thoracic duct.

5. The method of claim 1, wherein delivering the neural stimulation pulses comprises delivering the neural stimulation pulses through the first stimulation electrode and a second stimulation electrode placed in the one of the lymphatic vessels.

6. The method of claim 1, wherein delivering the neural stimulation pulses comprises delivering the neural stimulation pulses through the first stimulation electrode and a second stimulation electrode placed in a location in the body external the lymphatic vessels.

7. The method of claim 1, further comprising:
   sensing one or more physiological signals; and
   controlling the delivery of the neural stimulation pulses using the one or more physiological signals.

8. The method of claim 7, wherein sensing the one or more physiological signals comprises sensing a neural signal using the first stimulation electrode, and controlling the delivery of the neural stimulation pulses comprises controlling the delivery of the neural, stimulation pulses using the neural signal.

9. The method of claim 1, further comprising:
   controlling the delivery of the neural stimulation pulses using a plurality of stimulation parameters;
   receiving one or more values of the plurality of stimulation parameters; and
   storing the received one or more values of the plurality of the stimulation parameters.

10. The method of claim 9, further comprising programming one or more values of the stimulation parameters according to a target to which the neural stimulation pulses are delivered, the target including one or more component of a nervous system.

11. The method of claim 10, wherein delivering the neural stimulation pulses comprises delivering the neural stimulation pulses to a parasympathetic nerve.

12. The method of claim 11, wherein delivering the neural stimulation pulses comprises delivering the neural stimulation pulses to a vagus nerve.

13. The method of claim 10, wherein delivering the neural stimulation pulses comprises delivering the neural stimulation pulses to a sympathetic nerve.

14. The method of claim 10, wherein delivering the neural stimulation pulses comprises delivering the neural stimulation pulses to a spinal cord.

15. The method of claim 10, wherein delivering the neural stimulation pulses comprises delivering the neural stimulation pulses to baroreceptors.

16. The method of claim 1, wherein delivering the neural stimulation pulses comprises delivering the neural stimulation pulses to treat hypertension by baroreceptor stimulation.

17. The method of claim 1, wherein delivering the neural stimulation pulses comprises delivering the neural stimulation pulses to heart failure by sympathetic inhibition or vagal excitation.

18. The method of claim 1, wherein delivering the neural stimulation pulses comprises delivering the neural stimulation pulses to control post-myocardial infarction remodeling by sympathetic inhibition or vagal excitation.

19. The method of claim 1, wherein delivering the neural stimulation pulses comprises delivering the neural stimulation pulses to mitigate chronic pain by neural activation or blocking.

20. The method of claim 1, wherein delivering the neural stimulation pulses comprises delivering the neural stimulation pulses to treat vascular pain including refractory angina and peripheral vascular diseases (PVD) by spinal cord stimulation.

21. The method of claim 1, wherein delivering the neural stimulation pulses comprises delivering the neural stimulation pulses to treat rachidian pain, treat type 1 or type 2 chronic regional pain syndrome (CRPS) by spinal cord stimulation, treat perineal pain and urological diseases by spinal cord stimulation, or restore lower extremity motor functions after spinal cord injury by ventral spinal cord stimulation.

22. A method for delivering neural stimulation to a target region in a patient's body having a lymphatic system and a nervous system, the lymphatic system including a thoracic duct and vessels branching from the thoracic duct the lymphatic vessel and the target region not constantly in direct contact in their natural state, the method comprising:

providing an electrode assembly including an electrode base configured to be implanted into a lymphatic vessel and a first stimulation electrode on the electrode base, the electrode base configured to cause a portion of the lymphatic vessel to substantially alter its natural path to contact the target region, to maintain the contact between the portion of the lymphatic vessel and the target region, and to allow the first stimulation electrode to be in contact with an inner wall of the lymphatic vessel after an implantation of the electrode assembly; and delivering neural stimulation pulses to the target region through the first stimulation electrode after the electrode assembly is implanted in a location in the lymphatic vessel using the thoracic duct as a conduit for advancing the electrode assembly to the location to reduce invasiveness of a procedure for implantation of the electrode assembly wherein the location is adjacent to the target region, the target region is part of the nervous system, the lymphatic vessel is the thoracic duct or one of the vessels branching from the thoracic duct, and the neural stimulation pulses are delivered to treat one or more clinical conditions each associated with a physiological function regulated by the target region;

wherein the one or more clinical conditions is a respiratory disorder, abnormal blood pressure, cardiac arrhythmia, myocardial infarction, ischemic insult, heart failure, epilepsy, depression, renal disorders, pain, migraine, obesity, movement disorders, and incontinence.

23. The method of claim 22, wherein providing the electrode assembly comprises providing an electrode assembly including an elongate electrode base including one or more biases each configured to cause the portion of the lymphatic vessel to substantially alter its natural path to contact the target region, the elongate electrode base having a stiffness allowing for maintaining the contact between the portion of the lymphatic vessel and the target region after the implantation of the electrode assembly.

24. The method of claim 22, wherein providing the electrode assembly comprises providing an electrode assembly including an expandable electrode base configured to cause the portion of the lymphatic vessel to substantially alter its natural path to contact the target region after the expandable electrode base is expanded.

25. The method of claim 22, comprising delivering the neural stimulation pulses from an implantable medical device connected to the first stimulation electrode through an implantable lead.

26. The method of claim 25, comprising deliver neural stimulation pulses to the target region through the first stimulation electrode and a second stimulation electrode placed in a location external to the lymphatic vessel.

\* \* \* \* \*